United States Patent
Liebermann et al.

[11] Patent Number: 5,971,755
[45] Date of Patent: Oct. 26, 1999

[54] LASER INSTRUMENT

[75] Inventors: Bernd Liebermann, Weingarten; Alexander Hack, Biberach-Rissegg, both of Germany

[73] Assignee: Kaltenbach & Voigt GmbH & Co., Biberach, Germany

[21] Appl. No.: 08/918,877

[22] Filed: Aug. 26, 1997

[30] Foreign Application Priority Data

Sep. 6, 1996 [DE] Germany .................. 196 36 265

[51] Int. Cl.[6] .................................................. A61C 1/00
[52] U.S. Cl. ............................................ 433/29; 606/17
[58] Field of Search ................. 433/29, 229; 606/13, 606/15, 16, 17; 607/89

[56] References Cited

U.S. PATENT DOCUMENTS

| | | | |
|---|---|---|---|
| 1,542,183 | 6/1925 | Steinberg | 433/29 |
| 4,849,859 | 7/1989 | Nagasawa | 606/17 |
| 5,090,908 | 2/1992 | Teumin-Stone | 433/229 |
| 5,139,495 | 8/1992 | Daikuzono | 606/17 |
| 5,348,552 | 9/1994 | Nakajima et al. | 606/16 |
| 5,388,987 | 2/1995 | Badoz et al. | 433/29 |
| 5,616,141 | 4/1997 | Cipolla | 433/29 |
| 5,688,261 | 11/1997 | Amirkhanian et al. | 606/17 |

FOREIGN PATENT DOCUMENTS

| | | | |
|---|---|---|---|
| 375 578 | 6/1990 | European Pat. Off. | 433/29 |
| 523 506 | 1/1993 | European Pat. Off. | 433/29 |
| 38 40 609 A1 | 6/1990 | Germany . | |
| 40 30 734 A1 | 4/1991 | Germany . | |
| 40 38 809 C1 | 4/1992 | Germany . | |
| 5-095 954 | 4/1993 | Japan | 606/13 |

*Primary Examiner*—Ralph A. Lewis
*Attorney, Agent, or Firm*—Scully, Scott, Murphy & Presser

[57] ABSTRACT

In the case of a laser instrument (1) with a laser-light guiding device (3) feeding the laser light, an oblong outcoupling element (15), the longitudinal direction of which is arranged at an angle (W4) in relation to the direction with which the laser light emerges from the guiding device (3), and with a laser-light deflecting device (26) which introduces the laser light emerging from the guiding device (3) into the outcoupling element (15), the deflecting device (26) is integrally moulded onto the outcoupling element (15).

18 Claims, 2 Drawing Sheets

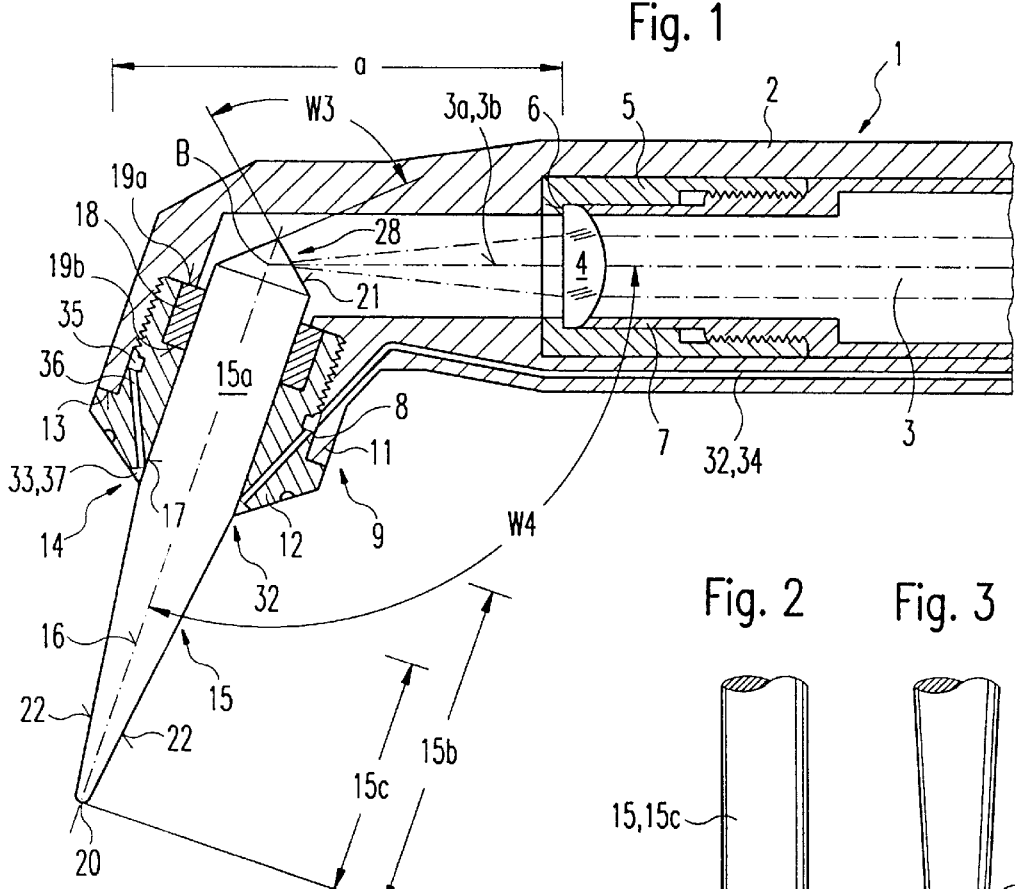
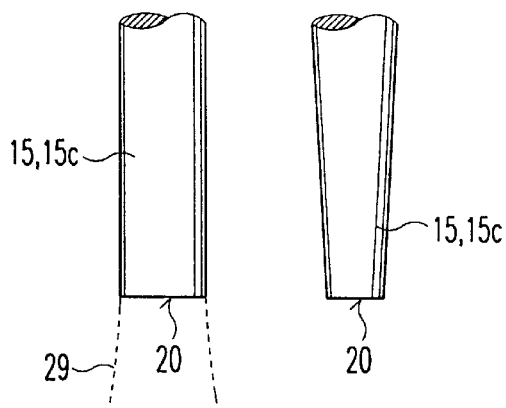
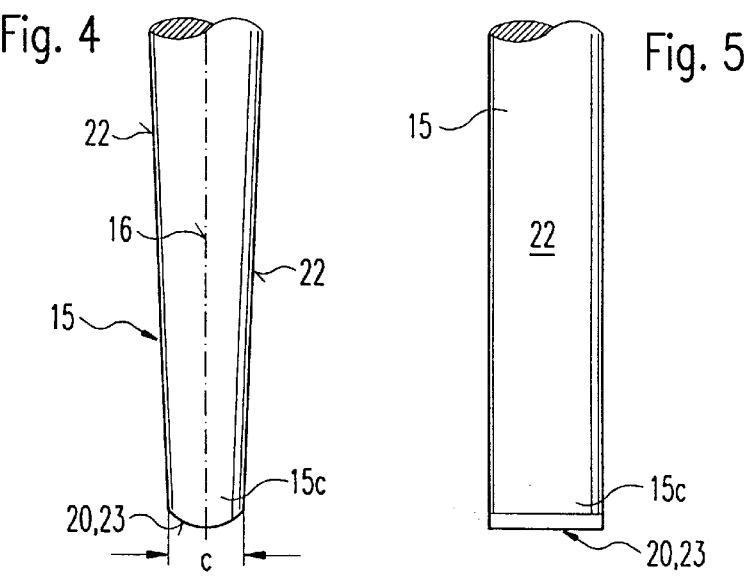
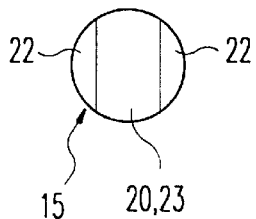

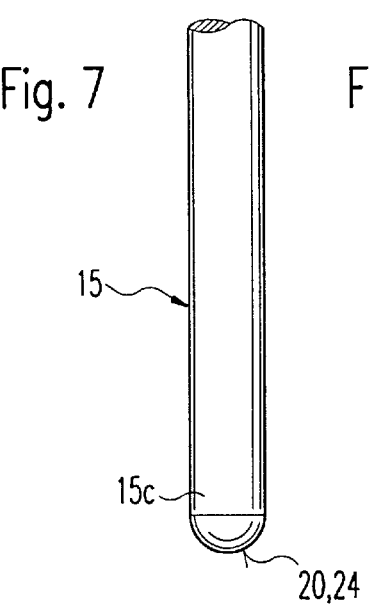
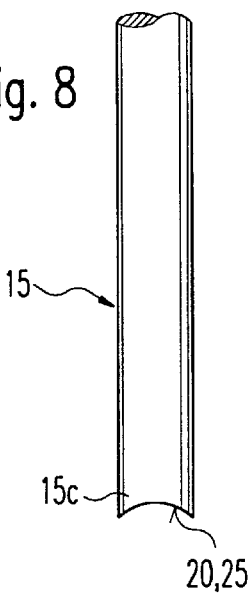
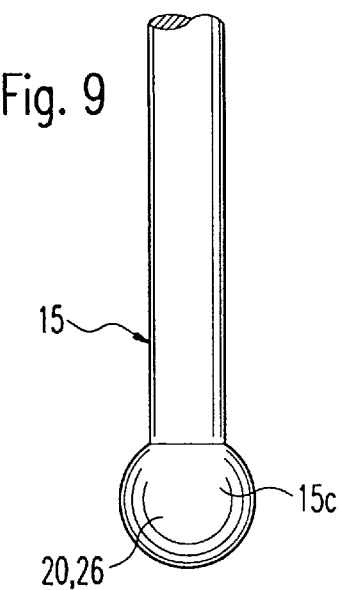
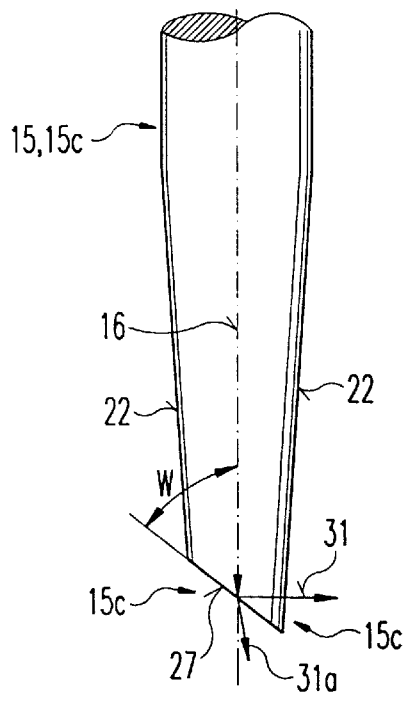
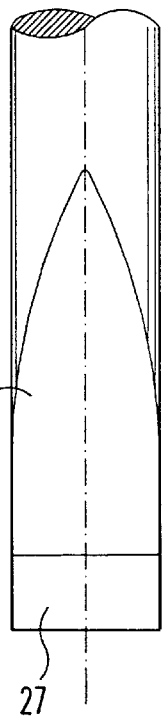
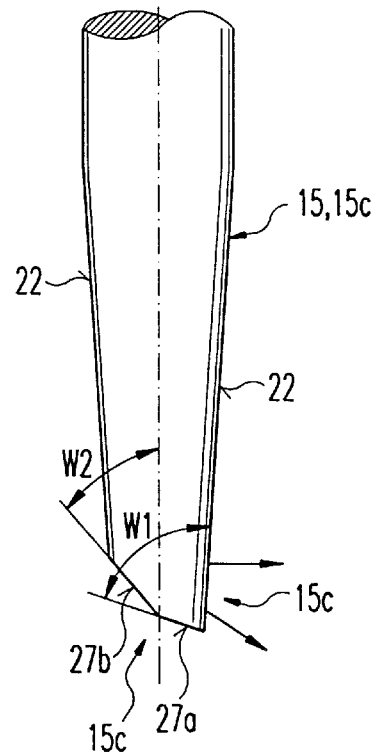

LASER INSTRUMENT

BACKGROUND OF THE INVENTION

1. Field of the Invention

The invention relates to a laser instrument with a laser light guiding device.

As regards style of construction, in the case of laser instruments one distinguishes between those wherein a laser outcoupling element extends in the longitudinal direction of a rod-shaped holding part and those in which the laser outcoupling element extends at right angles to the rod-shaped holding part.

The use of the laser instrument of the former type is restricted to applications in which the treatment point is surrounded by a large free space that is easily accessible, as is the case for example in the treatment with the laser instrument of the skin of the human body or the body of an animal. Such a laser instrument is described in DE 38 40 609 A1.

However, for ergonomic and visual reasons it is more advantageous to make use of a laser instrument having a laser outcoupling element extending at right angles to the rod-shaped holding part or handle part. Such a laser instrument can be comfortably held ergonomically with the operating hand, whereby the line of sight to the treatment point is improved, since it is directed at right angles to the center axis of the laser outcoupling element, or the laser instrument or the person conducting the treatment can carry out the work in such a position that the line of sight directed at right angles to the laser outcoupling element is favorable.

It becomes evident that not only the physical burden on the person conducting the treatment but also the quality of the work to be performed with the laser is dependent on a favorable structural shape of the laser instrument and also a favourable line of sight. In a favourable treatment position the person conducting the treatment can perform the work with reduced exertion and attentiveness, on the one hand more precisely and qualitatively better, and on the other hand for a longer time, since his/her physical powers are taxed to a lesser extent.

The aforementioned difficulties arise in particular at those treatment sites which are difficult to access, as is the case for example in body cavities and in particular in the oral cavity of the human body or the body of an animal. In such applications angular laser instruments are suitable—in effect, those structural types in which the laser outcoupling element is directed at right angles to the longitudinal center axis of the rod-shaped holding part or handle part. With such a laser instrument the emergent laser beam is directed transversely. By this means, on the one hand the access to various treatment sites in the body cavity is favorable, and on the other hand the laser instrument can both be held in ergonomically favorable manner and can be moved for the surgical operation and favorably observed. In this connection it should be taken into consideration that these activities have to be performed through the opening in the body cavity.

For the aforementioned reasons use is being made with increasing frequency of an aforementioned angular laser instrument for treatment both at treatment sites that are difficult to access and at easily accessible treatment sites. Although an angular laser instrument is more costly to produce, since it requires a deflection of the laser beams, the advantages described above outweigh this consideration.

In the following, a distinction has to be made between those laser instruments in which the laser outcoupling element is arranged in the holding part and those in which it protrudes from the holding part. With the former style of construction the laser radiation merely emerges from the holding part, in particular in focused form, towards a focal point or treatment point arranged at a certain spacing from the laser instrument. In the second case the laser radiation is also transmitted outside the holding part in the laser outcoupling element, whereby the outcoupling or the emergence of the laser beam takes place at the free end of the laser outcoupling element and whereby this free end can be brought right up to the tissue to be treated and, optionally, in addition to the irradiation a mechanical action can be exerted on the tissue with the laser outcoupling element.

2. Description of the Prior Art

A laser instrument of the type specified in the introduction is described in DE 40 30 734 A1 or in DE 40 38 809 C1.

The former printed publication presents a laser instrument which comprises on its front end a lateral angular extension, at the free end of which the laser radiation emerges in focused form through an exit aperture. With a view to deflecting the laser radiation, a mirror is provided in the angular region of the laser instrument. The laser outcoupling element is constituted by a lens which is arranged within the exit aperture in the laser instrument. Moreover, further optical elements for the purpose of guiding and transmitting the laser radiation in the laser instrument are provided.

In the second printed publication a dental laser instrument is described having a laser outcoupling element that protrudes laterally at the front end of a substantially straight holding part or handpiece and is held in the region of an exit aperture by means of a plug-in part. Within the handpiece a deflecting device for the laser beams is arranged upstream of the exit aperture, said deflecting device being constituted by a prism with an oblique refractive surface that faces away from the feed direction of the laser radiation. The surface of the prism that faces towards the laser radiation extends at a right angle to the feed direction of the laser radiation and parallel to the longitudinal center axis of the laser outcoupling element. At a distance from the prism in the rearward direction a lens is supported in the laser instrument or in the handle part so as to be axially displaceable, the purpose of which is to focus the laser radiation reaching the prism in such a way that use can be made of laser outcoupling elements of differing cross-sectional size—for example, a laser outcoupling element for an external dental treatment and a laser outcoupling element for a root-canal treatment.

SUMMARY OF THE INVENTION

One object underlying the invention is to configure a laser instrument of the type specified in such a way that a smaller and/or simpler style of construction is possible.

With the configuration according to the invention the deflecting device is constituted by the laser outcoupling element itself or is formed on the latter. As a result of this, not only does the deflecting device cease to be a separate component, but a smaller style of construction is also possible, since instead of a holder for the deflecting device and a holder for the laser outcoupling element; there is provided a common holder, as a result of which a simpler and smaller—and particularly shorter in the longitudinal direction of the outcoupling element—style of construction is achieved. A further advantage that can be attained with the configuration according to the invention consists in that the deflecting device is formed, and the laser transmission takes place, in the region of the outcoupling element on a one-piece component, and consequently on one and the same component, and therefore a higher degree of precision can be achieved, since deviations in connection with the holding of separate components, which are scarcely to be avoided as a result of tolerances, and deflections of the laser beam in the course of the interchange (exit and entry) of the media result in losses of laser transmission. In addition, with the configuration according to the invention the number of entries and exits of light into or out of the transmitting media is less and is restricted to one light guide. By this means additional tolerances of the angles of refraction are avoided. The configuration according to the invention consequently also reduces line losses and enables better utilization of the available radiant energy.

A further object underlying the invention is to configure a laser instrument of the type specified herein in such a way that its handling during the course of the treatment and, where appropriate, also its effectiveness is improved.

With this configuration according to the invention the outcoupling element is held in the holding part or handpiece of the laser instrument so as to be freely rotatable about an axis of rotation extending in its longitudinal direction. This configuration is advantageous for several reasons.

On the one hand, the outcoupling element is capable of being adjusted by manual twisting into optional rotary positions. By this means, optional peripheral-surface regions of the outcoupling element can be utilized. In addition, this configuration is advantageous with those outcoupling elements which have a circumferential surface or end face or light-exit face that differs from an axially symmetrical surface. In this connection a particular surface region of the outcoupling element can in each instance be rotated into a favorable rotary position with respect to the body site to be treated.

On the other hand, by virtue of the free rotary capacity of the outcoupling element no torque can be transmitted with the laser instrument to the treatment site—for example a tooth, a phenomenon which can lead to considerable loading or overloading of the tooth, for example. This configuration is suitable in particular for an outcoupling element having a non-circular cross-sectional shape, in particular a flat cross-sectional shape. With such a cross-sectional shape it is possible for a large and harmful torque by reason of the large leverage (handpiece length/cross-sectional dimension of the outcoupling element) to be transmitted with the laser instrument or handpiece to the treatment site or the tooth or within the interdental region. With the configuration according to the invention such a transmission of torque is ruled out. This configuration is also advantageous in the case of an outcoupling element having a circular cross-section, since harmful torques can also be transmitted with such a cross-sectional shape if the outcoupling element is not supported so as to be freely rotatable—for example when the outcoupling element is jammed between two teeth. Furthermore, the configuration according to the invention is advantageous with those outcoupling elements in which the free end surface of the outcoupling element deviates from an axially symmetrical shape. With such a shape, harmful pinching effects can also arise on the end surface if the outcoupling element is not supported so as to be freely rotatable.

A further advantage of this configuration according to the invention consists in the fact that the outcoupling element, by virtue of its free rotary capacity, is able to adapt itself automatically to the surface to be treated; for example, on the tooth or gum. This is the case when the outcoupling element has a lateral and/or end-sided surface that deviates from the axial symmetry of the outcoupling element. The effectiveness of the laser treatment is also particularly improved as regards this adaptability when the laser beams emerge on this surface or these surfaces. If the outcoupling element is able to adapt itself to, in each instance, the associated surface of the environment, then in each instance this results in a favorable installation and a favorable effective range for the laser beams emerging on this surface of the outcoupling element. On the other hand, in the case of an outcoupling element that is not supported so as to be freely rotatable, differing spacings of the laser-beam exit face on the outcoupling element arise with respect to the environment, as a result of which the effectiveness of the laser irradiation is impaired.

The transmission of laser light in the outcoupling element is preferably effected by utilising total reflection.

The specification discloses features which for additional reasons ensure a simple and small style of construction, enable an adaptation of the outcoupling element to differing positions of the object to be treated, improve the transmission of laser light and ensure an adjustment of the outcoupling element that is effortless as regards handling and also enable a configuration and mounting that can be produced at favorable cost.

Further features result in an improvement in effectiveness through the use of a particular laser radiation.

The laser instrument according to the invention can be employed very advantageously for the external treatment of teeth and of the gums, such as the removal of tartar coating and/or for a periodontosis treatment.

BRIEF DESCRIPTION OF THE DRAWINGS

The invention and other advantages that can be achieved with it are elucidated in more detail below on the basis of preferred configurations and drawings; in which there is shown in FIG. 1 the front end region of a medical or dental laser instrument in vertical longitudinal section;

FIG. 2 the free end region of a laser outcoupling element in the direction of view at right angles to its longitudinal axis;

FIG. 3 an outcoupling element in the direction of view at right angles to its longitudinal axis, in modified configuration;

FIG. 4 an outcoupling element in further modified configuration;

FIG. 5 a laser outcoupling element according to FIG. 4 in side view;

FIG. 6 the laser outcoupling element in bottom view;

FIG. 7 a laser outcoupling element in modified configuration;

FIG. 8 a laser outcoupling element in further modified configuration;

FIG. 9 a laser outcoupling element in further modified configuration;

FIG. 10 a laser outcoupling element in further modified configuration;

FIG. 11 the outcoupling element according to FIG. 10 in side view;

FIG. 12 the outcoupling element according to FIG. 10 in modified configuration.

DETAILED DESCRIPTION OF PREFERRED EMBODIMENTS

The laser instrument comprises a rod-shaped holding part preferably extending substantially in a straight line or at an angle, here in the form of a handpiece 1 which in its rear end region forms a handle part and comprises a gripping sleeve 2, along and through which a light-guiding channel 3 extends preferably in coaxial manner. The rear end of the laser handpiece, which is not represented, is capable of being connected by means of a coupling, in particular a plug-in/rotary coupling or a screw coupling, to a connecting piece that is connected by means of a flexible supply line to a control and supply device for energy and conventional media. A quick coupling described above with a cylindrical coupling recess and an encircling cylindrical coupling spigot therein is known per se. The laser feed is effected through the flexible line and through the coupling spigot into the light-guiding channel 3, which may be a free channel or a light guide that is inserted in the channel 3. At a spacing a from the front end of the laser handpiece 1 there is located in the light-guiding channel 3 a lens 4 which is fixed in a bushing 5 that is preferably inserted from the front into the gripping sleeve 2 between an inner shoulder 6 and a sleeve 7 which is preferably screwed into the bushing 5 from the front. In front of the lens 4 there is an open hollow space in the laser handpiece 1.

At the front end the laser handpiece 1 comprises a lateral opening 8, in the region of which a holding device 9 with a socket 14 for a laser outcoupling element 15 is arranged. The opening 8 is formed by a lateral sleeve bushing 11, into which an insert part or screw part 12 is inserted or screwed from outside which adjoins an annular stop 13 on the end face of the sleeve bushing 11 and is consequently axially fixed. Formed coaxially in the screw part 12 is the socket 14 in which the rod-shaped outcoupling element 15 is supported so as to be freely rotatable about its longitudinal axis 16 and axially non-displaceable. For this purpose use is made of a hollow cylindrical stepped bore 17 in which a cylindrical shaft 15a of the outcoupling element 15 and a radial holding projection 18 fastened thereto, here in the form of a hollow cylindrical holding ring, are received subject to movement clearance. The holding attachment 18 is held axially between shoulder faces 19a, 19b of the handpiece 1 and of the screw part 12 and is fastened detachably or non-detachably to the cylindrical shaft 15a of the outcoupling element 15, for example by adhesion-bonding or clamping or by being pressed on. The holding projection 18 may also be integrally moulded on the outcoupling element 15 and may consist of the same material.

The outcoupling element 15 consists of light-transmitting material such as glass or quartz, sapphire, crystal or plastic. It projects by the extent 15b of about 10 to 25 mm, in particular about 20 mm, from the handpiece 1, the free end region of this connecting shaft 15b forming, in a manner yet to be described, a treatment section 15c.

It is particularly advantageous to utilize a light-transmitting fiber for an outcoupling element 15 or to produce the outcoupling element from a light-transmitting fiber by way of starting-material. By this means a low-loss or loss-free transmission of laser light in the outcoupling element 15 is possible. In addition, losses are significantly reduced or avoided in the course of coupling the laser light into the outcoupling element. This is achieved through the conventional light-transmitting fiber consisting of a core and a jacket, the refractive indices of which are different. This results in a favorable numerical aperture, the transmission of light in the outcoupling element in the case of total reflection taking place on its circumferential surface and as a result being transmitted in substantially loss-free manner. With light-transmitting fibers this is known per se.

The upper or inner end of the outcoupling element 15 has a laser incoupling face 21 extending obliquely in relation to the longitudinal center axis 3a of the light-guiding channel 3 and obliquely in relation to the longitudinal center axis 16 of the outcoupling element 15, said laser incoupling face being arranged on the rearward-directed side of the outcoupling element 15 and consequently being directed rearwards or towards the light-guiding channel 3. The incoupling face 21 is preferably formed by a conical surface which, for example, may be ground or partly ground. The cross-sectional size of the preferably circular outcoupling element 15 is relatively small and amounts to about 0.6 to 3 mm, in particular about 2 mm, in diameter. By virtue of these small cross-sectional dimensions particular strength requirements are placed on the outcoupling element 15. It is therefore advantageous to configure the outcoupling element 15 to be convergent towards its free end so that in the region of the connecting shaft 15b and of the holding shaft 15a a larger cross-section is predetermined. In this shaft region the strength should be greater, since by virtue of a lever action in the course of the treatment this region is particularly subject to the risk of fracture.

The free end and/or the connecting shaft 15c of the outcoupling element 15 may exhibit various shapes that are adapted to a desired therapeutic measure. As will be described below, the laser instrument 1 or the outcoupling element 15 is outstandingly suitable for removing harmful coatings such as tartar and concretions from the jaw or gums or from the teeth and in particular in the region of the dental pockets. This is effected by means of laser irradiation which emerges in the free end region, in particular on the end face of the outcoupling element 15, and which destroys the coating, whereby said coating can be removed at the same time or in the course of subsequent cleaning.

For an external treatment of the teeth or the gums the outcoupling element 15 could be of uniform thickness in cross-section. For a treatment in the dental pockets the treatment section 15c should only be of such a size in cross-section that it is able to be introduced into the dental pocket. Since the dental pocket constitutes a gap, it is advantageous to form the outcoupling element 15 with an oblong cross-sectional shape in the region of the treatment section 15c or of the connecting shaft 15b so that it is adapted to the gap. This can be achieved with a wedge shape having wedge faces arranged on one or both sides which —viewed in cross-section—may be plane faces or slightly rounded faces. By virtue of this flat cross-sectional shape the outcoupling element 15 can be easily introduced into a dental pocket, whereby, depending on the desired depth of treatment, it can be introduced by a few mm. The free end face of the outcoupling element 15 with which it penetrates into the dental pocket may be of plane, convex or concave form. In this connection it may be a question of spherical or prismatic, convex or concave shapes, whereby in the case of an oblong cross-sectional shape the prismatic shape preferably extends parallel to the longitudinal direction of the oblong cross-sectional shape.

With the configuration according to FIG. 2 the free end region or connecting shaft 15b is cylindrical in form, it being possible for this cylindrical section to continue coaxially on a holding shaft 15a of the same or greater diameter. The free end face 20 may be a plane diametral face or an inclined face or a concavely rounded face or a wedge-shaped pointed face.

According to FIG. 3 the connecting shaft 15b is of conical construction, whereby the end face 20 may be diametrally plane or likewise inclined or convexly rounded or wedge-shaped. The cross-sectional dimension c of the end face 20 amounts to about 0.6 mm. The cross-sectional shape which is convergent towards the free end may also be formed by a flattening on one side or on both sides, as a result of which the free end region of the outcoupling element 15 receives a wedge-shaped or chisel-shaped form. By this means, at the free end a vertex is formed which extends in the longitudinal direction of the oblong cross-sectional shape.

With the configuration according to FIGS. 4 to 6 the free end is chisel-shaped with two convergent, approximately plane wedge faces 22 located opposite one another which do not come to a point but form a straight, relatively wide vertex 23, the end face 20 of which preferably exhibits the shape of a cylindrical section. The width of the vertex 23 corresponds approximately to one half of the cross-sectional dimension of the shaft 15*a*, preferably to the dimension c of about 0.6 mm. The end face or vertex face 23 may be plane or concavely rounded or have the shape of a pointed roof on one side or on both sides. The wedge faces form with the center axis 16 an angle of preferably about 2° or 2 to 8°.

According to FIG. 7 the free end of the outcoupling element 15 is cylindrical in form with a cylindrical-section-shaped, spherical or hemispherical dome 24.

With the configuration according to FIG. 8 the free end of the outcoupling element 15 comprises a partly cylindrical or spherical concave recess 25.

According to FIG. 9, at the free end of the outcoupling element 15 a rounded, in particular a globular, enlargement 26 is arranged, the cross-sectional dimension of which is larger than the cross-sectional dimension of the connecting shaft 15*b* bearing the enlargement.

With the configuration according to FIGS. 10 and 11 a cylindrical (FIG. 2) or conical (FIG. 3) or flattened wedge-shaped configuration (FIG. 4) is combined with a convex, prismatic shape of the treatment section 15*c*, the end face 20 being formed by an approximately concave or convexly rounded or plane oblique face 27 which forms with the wedge face 22 located opposite or with the longitudinal center axis 16 an angle W of 30 to 60 or 70°, in particular about 45°.

FIG. 12 shows a variant of the configuration according to FIG. 10. With this configuration the oblique face is formed by first and second oblique-face sections 27*a*, 27*b*. The first cross-sectional section 27*a* emanating from one side or wedge face 22 forms an angle W1 of about 60 to 90°, in particular 70°, whereas the second face section forms an angle of about 20 to 45°, in particular about 30°. The width d or the spacing thereof from the associated side amounts to approximately one half of the dimension c—for example, 0.2 to 0.3 mm.

By virtue of the small previously described dimensions and shapes the outcoupling element 15 is capable of being introduced not only in interdental regions but also in dental pockets between the gum and the base of the tooth. By virtue of the free rotary capacity of the outcoupling element 15 it is capable of being adapted to the respective working positions, and in this connection, particularly in the case of cross-sectional shapes that are not circular, pinching effects are ruled out that might be exerted on the teeth by a lever action transmitted with the laser handpiece 1 if the outcoupling element 15 were not supported so as to be rotatable.

The laser beams generally designated by 8 are focused onto the incoupling face 21 with the lens 4. The center axis 3*b* of the focused section is preferably directed coaxially in relation to the center axis 3*a* of the guiding device 3. A focal point may be located in the region of the center axis 16, in the region of the cone or in the region of, or on, the incoupling face 21. By virtue of the natural refraction of light the incoupling face 21 forms with the associated inner end region of the outcoupling element 15 a deflecting device 26 for the purpose of deflecting the laser beams towards the free end of the outcoupling element 15. By virtue of the conical or truncated conical shape of the incoupling face 21 a low-loss input coupling and deflection is ensured in every rotary position of the outcoupling element. The cone angle W3 is acute, right-angled or obtuse and preferably amounts to about 30 to 90°, in particular about 70°. The angle W4 formed by the center axes 3*a* and 16*c* may be acute, right-angled or obtuse and preferably amounts to about 90 to 155°, in particular about 110°.

In the outcoupling element 15 a total reflection of the laser beams preferably takes place on the circumferential surface thereof, so that the transmission of light in the outcoupling element 15 is effected without losses. With the present configuration this is ensured by the outcoupling element 15 preferably being formed by a conventional light-transmitting fiber or being manufactured from such a fiber, whereby the faces of the cone 28 varying from the cylindrical shape and the conical faces in the region of the connecting shaft 15*b* and light exit faces in the region of the treatment section 15*c* may be ground. The light-entry and light-exit faces are preferably polished.

However, within the scope of the invention it is also possible to bring about a total reflection in the outcoupling element 15 when the outcoupling element 15 does not consist of a light-transmitting fiber but of glass or quartz, sapphire, crystal or plastic. In this connection the angles W3, W4 should be of such a magnitude that, while taking into account the consequences of physical regularities such as the focusing angle of the lens 4 and the deflection of the light beam when the laser light enters the outcoupling element 15, total reflection takes place on the inner circumferential surface of the outcoupling element 15 in the course of the transmission of the laser light.

The advantageous mode of action of the invention in the case of destruction or elimination of previously described harmful coatings, particularly in the case of a periodontosis treatment in dental pockets, results from the application of an Er:YAG laser which is guided from the control and supply device through the flexible supply line through the coupling to the handpiece 1. In trials it has been shown that an Er:YAG laser light with a wavelength of about 2.94 $\mu$m and a pulse duration of about 200 to 400 $\mu$s, preferably about 300 $\mu$m, is highly suitable. In this connection advantageous results are achieved with a pulse energy of about 100 to 500 mJ. An associated laser generation device is preferably configured in such a way that the pulse power is variable and consequently adjustable. It has been shown that with an energy density of more than 0.8 J/cm$^2$ the harmful coatings can be destroyed and cleared away.

This function can be attributed to the fact that in the course of the laser irradiation of the coating by the laser light that emerges at the treatment section 15*c* and the relatively high absorption of the laser light that takes place in the process in the water located in the concretions, the water or the moisture that is present evaporates, as a result of which the concretions are cleared away and at least partly disintegrate into small particles.

In this connection the laser beam emerges at the distal end of the outcoupling element 15 in the region of the treatment instrument 15*c*. The convergent or divergent beam angle formed by the emergent laser beam and the homogeneity of the beam profile are determined by the transmission of light in the region of the outcoupling element 15, here by the numerical aperture of the light-transmitting fiber, and the shape of the exit face. It is advantageous to provide different outcoupling elements 15 which are adapted for a particular treatment situation and which are exchangeable. The holding device 10 that is present for the outcoupling element 15 is equipped for such an exchange.

In FIG. 2 the emergence of the laser beam from the end face 20 of the outcoupling element 15 is indicated by two boundary lines 29. The lines border a divergent laser beam.

With the configuration according to FIGS. 10 to 12 a particular exit of the laser beam is predetermined by virtue of the particular shaping. The rounded or plane oblique face 27 forms an inner reflection face on which the laser beam as a whole or a portion of the radiation is reflected laterally by virtue of total reflection, indicated by the arrows 31, 31a. For the following reasons the portions of the radiation 31a emerging at the face 27 and of the radiation 31 reflected laterally thereon can be determined by the magnitude of the angle W.

In connection with the transition of the laser beams at the face 27 a critical angle that is dependent on the material of the outcoupling element 15 is predetermined (in the case of glass, 41°), whereby when said critical angle is exceeded a total reflection takes place and the laser beams are reflected laterally on the face 27—see arrow 31. If, on the other hand, the critical angle is not attained, the laser beams (neglecting a reflected portion) emerge at the face 27 (arrow 31a). However, in reality the beam direction of the laser beams transmitted in the outcoupling element 15 does not extend axially parallel in relation to the center axis 16 but in the region of a certain angle of scattering. Depending on requirements it is therefore advantageous to choose the angle W to be of such a magnitude, taking into account the refractive index of the material and the scattering angle, that the laser beams emerge substantially only at the face 27 (arrow 31a) or emerge at the face 27 and are laterally reflected (arrow 31) or are only reflected laterally.

This is desirable in order to be able to treat tissue or coatings present in the region of the end face 20 and/or of the associated end-side region in each instance individually or simultaneously. In this connection the amount of irradiation energy that is active axially (31a) and/or laterally (31) can be determined by the magnitude of the angle W, or conversely the angle W3 is determined by a necessary amount of irradiation energy. This configuration is suitable in particular for treatment in a dental pocket. In this connection it is possible, in each instance individually or at the same time, to irradiate two adjacent regions of the dental pocket—for example, the surface of the base of the tooth and the adjacent pocket face—and to eliminate coatings or to remove the epithelium of the pocket.

The above statements apply correspondingly to the configuration according to FIG. 12. With this configuration the axially emergent radiation can be shifted or concentrated laterally into the region of the face 27b.

With all the configurations described above the edges of the treatment section 15c are slightly rounded, in order to treat the tissue with care.

It is advantageous to provide the therapeutic laser instrument or handpiece 1 with a feed device 32 for a treatment liquid, in particular water, whereby the at least one outlet aperture 33 of said feed device is directed towards the treatment site. By this means it is possible to supply treatment liquid and thereby keep the climate in the region of the treatment site and also the coatings or concretions sufficiently damp, as a result of which the previously described eliminating action is improved and/or the particles that have been cleared away are flushed out. In this connection it has been shown that relatively little treatment liquid is required and needs to be supplied, at any rate less than is the case with conventional dental drilling instruments. In trials the supply of a quantity of treatment liquid of about 4 ml/min has proved advantageous.

The feed device 32 comprises a feed channel 34 which extends along and through the handpiece 1 into the region of the lateral exit and which is fed by a feed line, that is not shown, in the flexible supply line which passes through the previously described coupling to the handpiece 1. The feed channel 34 extends to the outlet aperture 33, which may be one or more apertures that may be arranged in distributed manner around the outcoupling element 15. With the present configuration the feed channel 34 opens into a peripheral groove 35 between the insert part 12 and the sleeve bushing 11. From the peripheral groove 35 one or more channels 36, arranged in distributed manner, extend to the front edge of the insert part 12 that surrounds the outcoupling element 15, where they open out in the vicinity of, or preferably on, the outcoupling element 15 or on the inner surface of the hole 17 that receives it. By this means it is ensured that the treatment liquid flows along the surface of the outcoupling element 15. This is desirable in order to conduct the treatment liquid in targeted manner to the treatment site at the free end of the outcoupling element 15. With the present configuration there is provided at the front edge of the insert part 12 an annular groove 37 which adjoins the hole 17 and into which the channels 36 open.

In the outcoupling element 15 a total reflection of the laser beams preferably takes place.

We claim:

1. A laser instrument with a handgrip (1); a laser light guiding device (3) arranged within said handgrip for conducting laser light; an elongated laser light outcoupling element (15) located forwardly of said laser light guiding device and extending in a longitudinal direction which is arranged at an angle (W4) relative to the direction of which the laser light emerges from the guiding device (3); and a laser light deflecting device (28) which introduces the laser light emerging from the guiding device (3) into the outcoupling element (15), said deflecting device (28) being integrally formed with the outcoupling element (15), wherein on an end of the outcoupling element (15) facing the guiding device (3) or on the side of the outcoupling element (15) facing the guiding device (3) there is arranged a laser light incoupling face (21), said incoupling face (21) being selectively formed by a conical face or a truncated conical face.

2. A laser instrument as claimed in claim 1, wherein said outcoupling element (15) is a pin-shaped element which protrudes laterally from the handgrip (1), said outcoupling element (15) being supported so as to be freely rotatable about a longitudinal axis (16) of said outcoupling element, and wherein a free end region of the outcoupling element (15) possesses an elongate cross-sectional shape.

3. A laser instrument as claimed in claim 1 or 2, wherein the guiding device (3) and of the outcoupling element (15) each have a center axis (3a, 16) which subtend an angle (W4) of about 90° to 130°.

4. A laser instrument as claimed in claim 3, wherein the angle (W4) is about 110°.

5. A laser instrument as claimed in claim 1 or 2, wherein a free end region of the outcoupling element (15) has a cross-sectional size so as to be capable of being introduced into a dental pocket.

6. A laser instrument as claimed in claim 1 or 2, wherein the outcoupling element (15) possesses a cylindrical cross-sectional shape comprising a holding shaft (15a) retained in a holding device (4) in a leading end portion of said instrument or in a protruding shaft region (15b) extending from said holding device.

7. A laser instrument as claimed in claim 1 or 2, wherein an end face (23) of the outcoupling element (15) is selectively convex, concave, planar, spherical or prismatic in transverse extent.

8. A laser instrument as claimed in claim 1 or 2, wherein a free end region of the outcoupling element (15) is convergent on one or both sides thereof in the form of a wedge, and the convergence ends in a end face (23).

9. A laser instrument as claimed in claim 1 or 2, wherein a free end face (23) of the outcoupling element (15) is selectively rounded, rooflike or is formed by a oblique face (27) on one or both sides thereof.

10. A laser instrument as claimed in claim 9, wherein an angle (W) formed by the face (27) and a center axis (16) of the outcoupling element (15) is selected to be of a magnitude, taking into account the refractive index of the material of the outcoupling element (15) and a scattering angle with which laser beams transmitted in the outcoupling element (15) are able to impinge on the face (27) such that a substantial portion of the laser beams are radiated away (31a) on the face (27) and/or the laser beams are reflected laterally (31).

11. A laser instrument as claimed in claim 9, wherein the oblique face (27) is formed by a first face portion (27a) and a second face portion (27b), the second face portion (27b) possessing a progressive slope relative to the first face portion (27a).

12. A laser instrument as claimed in claim 9, wherein the oblique face (27) is located opposite a lateral flattening of the outcoupling element (15).

13. A laser instrument as claimed in claim 1 or 2, wherein a feed device (32) comprising channel means (34) formed in said handpiece is operatively connected thereto for conveying a treatment liquid such as water, to at least one or more outlet apertures (33) of said feed device directed towards a treatment site.

14. A laser instrument as claimed in claim 13, wherein the outlet aperture or the outlet apertures (33) lead out of an edge region of the holding part (1) which surrounds the outcoupling element (15) in a region adjoining the circumferential surface of the outcoupling element (15) or on a wall of an aperture (17) for the receiving thereof.

15. A laser instrument as claimed in claim 1, wherein the incoupling face (21) is formed by a conically convergent rotationally symmetrical incoupling face.

16. A laser instrument as claimed in claim 1, wherein a cone angle (W3) of the conical face or truncated conical face is in the range of about 30° to 90°.

17. A laser instrument as claimed in claim 16, wherein the cone angle (W3) is about 70°.

18. A laser instrument as claimed in claim 1, wherein the incoupling face (21) extends within an angular range from approximately a right-angle to oblique relative a center axis (3a) of the guiding device (3) and obliquely relative to a center axis (16) of the outcoupling element (15).

* * * * *